US00PP08980P

United States Patent [19]

Glicenstein

[11] Patent Number: Plant 8,980

[45] Date of Patent: Nov. 15, 1994

[54] CHRYSANTHEMUM PLANT NAMED SUNNY DENISE

[75] Inventor: Leon Glicenstein, Salinas, Calif.

[73] Assignee: Yoder Brothers, Inc., Barberton, Ohio

[21] Appl. No.: 168,174

[22] Filed: Dec. 17, 1993

[51] Int. Cl.[5] ..... A01A 5/00

[52] U.S. Cl. ..... Plt./78

[58] Field of Search ..... Plt. 76, 78

[56] References Cited

U.S. PATENT DOCUMENTS 4,616,099 10/1986 Sparkes ..... 47/58

OTHER PUBLICATIONS

Broertjes, et al., 1980, "A mutant of a mutant of a . . . Irradiation of progressive radiation-induced mutations in a mutation breeding programme with *Chrysanthemum morifolium*", Euphytica, 29:526–530.

Gosling, ed., 1979, "The Chrysanthemum Manual—6th Edition", The National Chrysanthemum Society, London, Essex Telegraph Press, Ltd., pp. 329–336.

Broertjes, et al., 1978, "Application of Mutation Breeding Methods in the Improvement of Vegitatively Propagated Crops", Elsevier Sci. Pub. Co., New York, pp. 162–175.

Searle, et al., 1968, "Chrysanthemums the Year Round", Blanford Press, London, pp. 27–29, 320–327.

Chan, 1966, "Chrysanthemum and rose mutations induced by X-rays", Am. Soc. Hort. Sci. Proc., pp. 613–620.

Broertjes, 1966, "Mutation breeding of Chrysanthemums", Euphytica, 15:156–162.

Dowrick, et al., 1966, "The induction of mutations in Chrysanthemum using X- and gamma radiation", Euphytica, 15:204–210.

*Primary Examiner*—Howard J. Locker

*Attorney, Agent, or Firm*—Foley & Lardner

[57] ABSTRACT

A Chrysanthemum plant named Sunny Denise particularly characterized by its flat capitulum form; spooned decorative capitulum type; bright yellow ray floret color; diameter across face of capitulum of 76 to 89 mm when fully opened; branching pattern is spreading and prolific, with 6 to 9 breaks after pinch when grown outside under natural daylength in fall flowerings, and 6 to 7 breaks after pinch when grown in 10 cm pots for spring flowerings; natural season flower date of August 25 to September 3 when planting rooted cuttings on June 21 to June 23 in Salinas, Calif., and September 30 when planting rooted cuttings June 11 in Hightstown, N.J.; flowering response of 45 to 49 days after rooting in no light/no shade programs in spring; plant height of 33 cm when grown in fall under natural daylength with no growth regulators in New Jersey, 25 to 30 cm when grown in fall under natural daylength in California, and 21 cm when grown in 10 cm pots in spring with no applications of 2500 ppm B-9 SP; and durable, uniform performance.

1 Drawing Sheet

The present invention comprises a new and distinct cultivar of Chrysanthemum, botanically known as *Dendranthema grandiflora,* and referred to by the cultivar name Sunny Denise.

Sunny Denise, identified as 8032 (88-308H01), is a product of a mutation induction program. The new cultivar was discovered and selected by Leon Glicenstein on Jul. 8, 1991, in a controlled environment in Salinas, Calif., as one flowering plant within a flowering block established as rooted cuttings from stock plants which had been exposed as unrooted cuttings to an X-ray source of 1750 rads in Fort Myers, Fla., on Mar. 21, 1991.

The irradiated parent cultivar was the cultivar identified as Denise, disclosed in U.S. Plant Pat. No. 8,178, described as a garden mum with a flat spooned decorative flower; greyed-orange ray floret color; diameter across face of capitulum of 76 to 89 mm when fully opened; spreading and prolific branching pattern, with 6 to 9 breaks after pinch when grown outside under natural daylength in fall flowerings, and 5 to 8 breaks after pinch when grown in 10 cm pots for spring flowerings; natural season flowering date of August 25 to 31 when planting rooted cuttings June 21 to 23 in Salinas, Calif., and September 30 to October 15 when planting rooted cuttings June 11 to June 18 in Hightstown, N.J.; flowering response of 45 to 49 days after rooting in no light/no shade programs in spring; plant height of 30 to 41 cm when grown in fall under natural daylength with no growth regulators in New Jersey, 25 to 30 cm when grown in fall under natural daylength with no growth regulators in California, and 21 to 25 cm when grown in 10 cm pots in spring with 0 to 2 applications of 2500 ppm B-9 SP. The ranges of measurements for Denise given here are wider than the measurements given in the description for Denise in the plant patent. This is based on continuing flowering trials of Denise after filing the plant patent application for Denise.

The irradiation program resulting in Sunny Denise had as its primary objective the expansion of color ranges of the parent cultivar Denise. The irradiation program comprised irradiating cuttings of the parent cultivar at irradiation levels of 1500, 1750 and 2000 rads. A total of 1299 cuttings harvested from a total of 225 irradiated plants were planted on May 13, 1991, May 6, 1991 and May 6, 1991, respectively. Of these, 26 initial selections were made, which selections were then revegetated and reflowered. Three consecutive flowerings resulted in discarding 20 of the original 26 selections on Mar. 19, 1992. Two codes were reselected, which reselections were ultimately discarded on Nov. 10, 1992. The remaining six selections were maintained as PIs (Possible Introductions) and further trialed in Salinas, Calif., Hightstown, N.J. and Leamington, Ontario, Canada, ultimately resulting in the decision to discard four of these codes on Oct. 1, 1992 and to introduce selection 8032 as Sunny Denise and selection 8019 as Autumn Denise. Autumn Denise is disclosed in pending Plant patent application Ser. No. 08/143,155.

The first act of asexual reproduction of Sunny Denise was accomplished when vegetative cuttings were taken from the initial selection in September 1991 in a controlled environment in Salinas, Calif., by technicians working under supervision of Leon Glicenstein.

Horticultural examination of controlled flowerings of successive plantings has shown that the unique combination of characteristics as herein disclosed for Sunny Denise are firmly fixed and are retained through successive generations of asexual reproduction.

Sunny Denise has not been observed under all possible environmental conditions. The phenotype may vary significantly with variations in environment such as temperature, light intensity and daylength, without, however, any variation in genotype.

The following observations, measurements and comparisons describe plants grown in controlled open areas in Salinas, Calif., and in Hightstown, N.J. Rooted cuttings were established in soil and maintained outdoors under the natural temperature and daylength prevailing during June through October. Spring flowerings were conducted in Salinas, Calif. under greenhouse conditions which approximate those generally used in commerical greenhouse practice for small pot spring garden mum production.

The following traits have been repeatedly observed and are determined to be basic characteristics of Sunny Denise, which, in combination, distinguish this Chrysanthemum as a new and distinct cultivar:

1. Flat capitulum form.
2. Spooned decorative capitulum type.
3. Bright yellow ray floret color.
4. Diameter across face of capitulum of 76 to 89 mm when fully opened.
5. Branching pattern is spreading and prolific, with 6 to 9 breaks after pinch when grown outside under natural daylength in fall flowerings, and 6 to 7 breaks after pinch when grown in 10 cm pots for spring flowerings.
6. Natural season flower date of August 25 to September 3 when planting rooted cuttings on June 21 to June 23 in Salinas, Calif., and September 30 when planting rooted cuttings June 11 in Hightstown, N.J.
7. Flowering response of 45 to 49 days after rooting in no light/no shade programs in spring.
8. Plant height of 33 cm when grown in fall under natural daylength with no growth regulators in New Jersey, 25 to 30 cm when grown in fall under natural daylength in California, and 21 cm when grown in 10 cm pots in spring with no applications of 2500 ppm B-9 SP.
9. Durable, uniform performance.

The accompanying photographic drawing is a color photograph of Sunny Denise grown as a pinched garden mum under natural season outside conditions in Salinas, Calif., with the colors being as nearly true as possible with illustrations of this type. Plants were grown outside and dug and transplanted into 15 cm bulb pans at flowering time for photography purposes.

Of the commercial cultivars known to the inventor, the most similar in comparison to Sunny Denise is the parent cultivar Denise. In the above description of Sunny Denise the ranges of values for Sunny Denise are much narrower than the ranges of values given for Denise. This is based on the fact that Denise was flowered over many years, while Sunny Denise was flowered over a period of only one and a half years. All traits of Sunny Denise are similar to those of Denise, except for the ray floret color. The ray floret color of Sunny Denise is bright yellow, while the ray floret color of Denise is greyed-orange.

In the following description color references are made to the Royal Horticultural Society Colour Chart. The color values were determined on plant material grown as a pinched garden mum grown under natural season outside conditions in Salinas, Calif. on Aug. 30, 1993.

Classification:

*Botanical.*—*Dendranthema grandiflora* cv Sunny Denise.

*Commerical.*—Flat spooned decorative spray pot mum and garden mum.

INFLORESCENCE

A. Capitulum:

*Form.*—Flat.

*Type.*—Spooned decorative.

*Diameter across face.*—76 to 89 mm when fully opened.

B. Corolla of ray florets:

*Color (general tonality from a distance of three meters).*—Bright yellow.

*Color (upper surface).*—Petal tips of outer petals 5B to 5C. Inner petals 6A.

*Color (under surface).*—6C.

*Shape.*—Spooned, with large section of the ray floret flattened and spoon-like, giving the impression of a decorative capitulum type.

C. Corolla of disc florets:

*Color (mature).*—14B.

*Color (immature).*—144B.

D. Reproductive organs:

*Androecium.*—Present on disc florets only, no to very scant pollen.

*Gynoecium.*—Present on both ray and disc florets.

PLANT

A. General appearance:

*Height.*—33 cm when grown in fall under natural daylength with no growth regulators in New Jersey, 25 to 30 cm when grown in fall under natural daylength in California, and 21 cm when grown in 10 cm pots in spring with no applications of 2500 ppm B-9 SP.

*Branching pattern.*—Spreading and prolific, with 6 to 9 breaks after pinch when grown outside under natural daylength in fall flowerings, and 6 to 7 breaks after pinch when grown in 10 cm pots for spring flowerings.

B. Foliage:

*Color (upper surface).*—147A.

*Color (under surface).*—147B.

I claim:

1. A new and distinct Chrysanthemum plant named Sunny Denise, as described and illustrated.

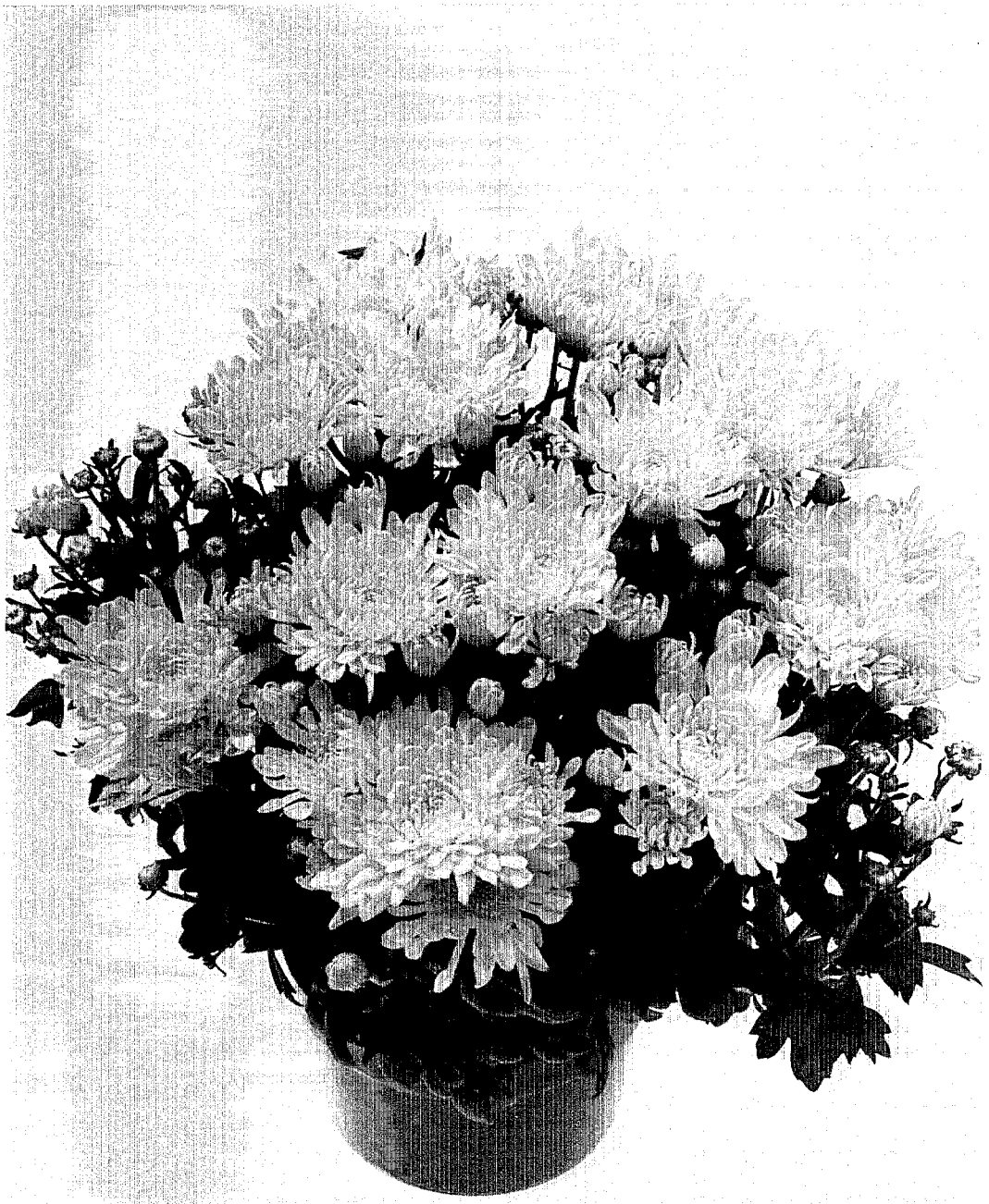

* * * * *